US00PP34328P2

(12) United States Plant Patent
Mekada et al.

(10) Patent No.: US PP34,328 P2
(45) Date of Patent: Jun. 14, 2022

(54) ***HYDRANGEA* PLANT NAMED 'FRCK 003 S 9'**

(50) Latin Name: ***Hydrangea macrophylla* X *Hydrangea hybrida***
Varietal Denomination: FRCK 003 S 9

(71) Applicants: Hiroyuki Mekada, Shimane (JP); Hiroko Inamura, Shimane (JP); Tetsuya Kako, Shimane (JP); Yuka Shimizu, Shimane (JP)

(72) Inventors: Hiroyuki Mekada, Shimane (JP); Hiroko Inamura, Shimane (JP); Tetsuya Kako, Shimane (JP); Yuka Shimizu, Shimane (JP)

(73) Assignee: SHIMANE PREFECTURE, Matsue (JP)

( * ) Notice: Subject to any disclaimer, the term of this patent is extended or adjusted under 35 U.S.C. 154(b) by 0 days.

(21) Appl. No.: 17/506,321

(22) Filed: Oct. 20, 2021

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

PUBLICATIONS

CPVO Register. https://online.plantvarieties.eu/public-ConsultationDetails?registerId=20203425&denomination=frck%20003%20s%209. 2 pages (Year: 2021).*

* cited by examiner

*Primary Examiner* — Karen M Redden
(74) *Attorney, Agent, or Firm* — C. Anne Whealy

(57) ABSTRACT

A new and distinct cultivar of *Hydrangea* plant named 'FRCK 003 S 9', characterized by its relatively compact and uniformly mounding plant habit; freely branching habit; strong and sturdy stems; freely flowering habit; large and dense mophead inflorescences with numerous double-type sterile flowers that can be "blued"; and good post-production longevity.

1 Drawing Sheet

Figure 1:
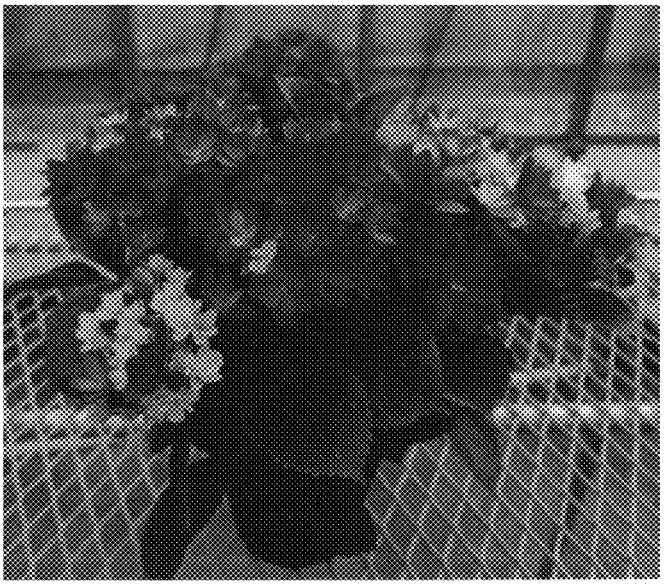

Botanical designation: *Hydrangea macrophylla* X *Hydrangea hybrida.*

Cultivar denomination: 'FRCK 003 S 9'.

CROSS-REFERENCED TO CLOSELY RELATED APPLICATIONS

Title: *Hydrangea* Plant Named 'FRCK 003 S 123'
First Named Inventor/Applicant: Hiroyuki Mekada
Filed: Concurrently with the instant application

STATEMENT REGARDING PRIOR DISCLOSURES BY INVENTOR/APPLICANT

A Japanese Plant Breeder's Rights application for the instant plant was filed by the Assignee, Shimane Prefecture of Shimane, Japan on Jun. 22, 2020, application number 34777. Foreign priority is not claimed to this application.

The Inventors/Applicants and Assignee assert that no publications nor advertisements relating to sales, offers for sale or public distribution occurred more than one year prior to the effective filing date of this application. Any information about the claimed plant would have been obtained from a direct or indirect disclosure from the Inventors/Applicants and/or the Assignee. Inventors/Applicants and Assignee claim a prior art exception under 35 U.S.C. 102(b)(1) for sales prior to the filing date but less than one year prior to the effective filing date.

BACKGROUND OF THE INVENTION

The present invention relates to a new and distinct cultivar of *Hydrangea* plant, botanically known as *Hydrangea macrophylla* X *Hydrangea hybrida*, commercially referred to as a Mophead *Hydrangea* and hereinafter referred to by the name 'FRCK 003 S 9'.

The new *Hydrangea* plant is a product of a planned breeding program conducted by the Inventors in Izumo-shi, Shimane, Japan. The objective of the breeding program is to create new freely-branching *Hydrangea* plants with compact plant habit and large inflorescences with double-type sterile flowers.

The new *Hydrangea* plant originated from a self-pollination made by the Inventors in June, 2010 in Izumo-shi, Shimane, Japan, of a proprietary selection of *Hydrangea macrophylla* X *Hydrangea hybrida* identified as code number FRCK-003, not patented. The new *Hydrangea* plant was discovered and selected by the Inventors as a single flowering plant from within the progeny of the stated self-pollination in a controlled greenhouse environment in Izumo-shi, Shimane, Japan in April, 2015.

Asexual reproduction of the new *Hydrangea* plant by vegetative tip cuttings in a controlled environment in Izumo-shi, Shimane, Japan since January, 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'FRCK 003 S 9'. These characteristics in combination distinguish 'FRCK 003 S 9' as a new and distinct *Hydrangea* plant:

1. Relatively compact and uniformly mounding plant habit.
2. Freely branching habit.
3. Strong and sturdy stems.
4. Freely flowering habit.
5. Large and dense mophead inflorescences with numerous double-type sterile flowers that can be "blued".
6. Good post-production longevity.

Plants of the new *Hydrangea* can be compared to plants of the parent selection. Plants of the new *Hydrangea* differ primarily from plants of the parent selection in inflorescence and flower form. Plants of the new *Hydrangea* have mophead inflorescences with double-type sterile flowers whereas plants of the parent selection have lacecap inflorescences with single-type sterile flowers.

Plants of the new *Hydrangea* can be compared to plants of the *Hydrangea macrophylla* X *Hydrangea hybrida* 'FRCK 003 S 123', disclosed in a U.S. Plant patent application Ser. No. 17/506,251 filed concurrently, primarily in sterile flower color. When "blued", plants of the new *Hydrangea* have blue-colored sterile flowers whereas plants of 'FRCK 003 S 123' have violet blue and white bi-colored sterile flowers. In addition, plants of the new *Hydrangea* have mophead-type inflorescences whereas plants of 'FRCK 003 S 123' have lacecap-type inflorescences.

Plants of the new *Hydrangea* can be compared to plants of the *Hydrangea macrophylla* 'Akanegumo', not patented. In side-by-side comparisons, plants of the new *Hydrangea* differ primarily from plants of 'Akanegumo' in the following characteristics:

1. Plants of the new *Hydrangea* have fewer lenticels on the stems than plants of 'Akanegumo'.
2. Plants of the new *Hydrangea* have darker green-colored leaves than plants of 'Akanegumo'.
3. Plants of the new *Hydrangea* flower later than plants of 'Akanegumo'.
4. Plants of the new *Hydrangea* have larger inflorescences with more sterile flowers than plants of 'Akanegumo'.
5. Sterile flowers of plants of the new *Hydrangea* are double-types whereas sterile flowers of plants of 'Akanegumo' are single-types.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph at the top of the sheet (FIG. 1) is a side perspective view of a typical flowering plant of 'FRCK 003 S 9' grown in a container.

Figure 2:
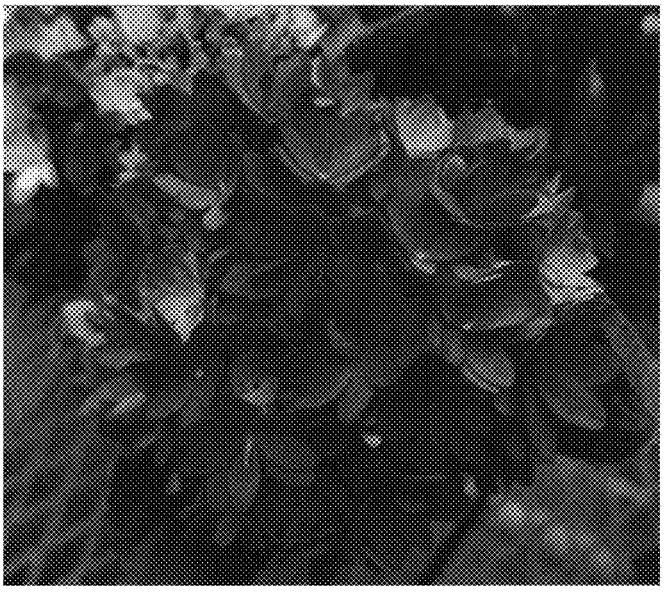

The photograph at the bottom of the sheet (FIG. 2) is a close-up view of a typical inflorescence of 'FRCK 003 S 9'.

DETAILED BOTANICAL DESCRIPTION

Plants used in the aforementioned photographs and in the following description were grown in containers in an outdoor nursery in Izumo-shi, Shimane, Japan and under cultural practices typical of commercial *Hydrangea* production. During the production of the plants, day temperatures ranged from about 15° C. to 25° C. Plants of the new *Hydrangea* were not pinched and were about twelve months from planting rooted young plants when the photographs were taken and about three months from planting rooted young plants when the description was taken. Plants of the new *Hydrangea* are suitable to be treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* X *Hydrangea hybrida* 'FRCK 003 S 9'.

Parentage:

*Female, or seed, parent*.—Proprietary selection of *Hydrangea macrophylla* X *Hydrangea hybrida* identified as code number FRCK-003, not patented.

*Male, or pollen, parent*.—Proprietary selection of *Hydrangea macrophylla* X *Hydrangea hybrida* identified as code number FRCK-003, not patented.

Propagation:

*Type cutting*.—By vegetative tip cuttings.

*Time to initiate roots, summer*.—About 30 days at temperatures about 15° C. to 25° C.

*Time to produce a rooted young plant, summer*.—About 90 days at temperatures about 15° C. to 25° C.

*Root description*.—Medium in thickness, fibrous; typically white to light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Relatively compact and uniformly mounded plant habit; upright and broadly outwardly spreading plant form; moderately vigorous growth habit and moderate growth rate.

*Plant height*.—About 25 cm.

*Plant diameter or area of spread*.—About 30 cm.

Lateral branch description:

*Branching habit*.—Freely branching habit with about four lateral branches per plant; pinching enhances lateral branch development.

*Length*.—About 10 cm to 12 cm.

*Diameter*.—About 4 mm.

*Internode length*.—About 3 cm.

*Strength*.—Strong, rigid.

*Aspect*.—About 45° from vertical.

*Texture*.—Smooth, glabrous; fully developed, woody.

*Color, developing*.—Close to 187B and at the internodes, close to 141C.

*Color, fully developed*.—Close to 187B and at the internodes, close to 139C; woody, close to 160D.

*Lenticels*.—Density: Sparse. Length: About 1 mm. Width: About 0.5 mm. Color: Close to 187B.

Leaf description:

*Arrangement*.—Opposite, simple.

*Length*.—About 7.8 cm.

*Width*.—About 5.2 cm.

*Shape*.—Ovate.

*Apex*.—Acuminate.

*Base*.—Acute.

*Margin*.—Coarsely serrate.

*Texture and luster, upper surface*.—Smooth, glabrous; glossy.

*Texture and luster, lower surface*.—Smooth, glabrous; matte.

*Venation pattern*.—Pinnate, reticulate.

*Color*.—Developing leaves, upper surface: Close to N134B. Developing leaves, lower surface: Close to 138B. Fully developed leaves, upper surface: Close to 137A; venation, to 148B. Fully developed leaves, lower surface: Close to 146B; venation, close to 145B.

*Petioles*.—Length: About 2 cm. Diameter: About 1 cm. Texture and luster, upper and lower surfaces: Smooth, glabrous; matte. Color, upper surface: Close to 145C. Color, lower surface: Close to 145A.

Flower description:

*Flower type and habit*.—Showy rotate and double sterile flowers and small, inconspicuous rotate fertile flowers arranged on mophead-type terminal panicles; panicles semi-globular in shape; sterile flowers face upright to outwardly depending on position on inflorescence and fertile flowers mostly upright.

*Fragrance*.—None detected.

*Natural flowering season*.—In the garden, plants flower in the early summer in Japan; plants begin flowering about 65 days after planting rooted young plants.

*Flower longevity*.—Good postproduction longevity; fertile flowers last for about 50 days on the plant and sterile flowers last for about 15 weeks on the plant; flowers persistent.

*Quantity of flowers*.—Freely flowering habit; about 85 sterile flowers per panicle and about 135 fertile flowers per panicle.

*Panicle height*.—About 7 cm.

*Panicle diameter*.—About 15 cm.

*Fertile flower buds*.—Length: About 2 mm. Diameter: About 1 mm. Shape: Globose. Color: Close to 144B.

*Sterile flower buds*.—Length: About 2 mm. Diameter: About 1 mm. Shape: Globose. Color: Close to 144B.

*Fertile flower diameter*.—About 2 mm.

*Fertile flower depth* (*height*).—About 3 mm.

*Sterile flower diameter*.—About 3.9 cm.

*Sterile flower depth* (*height*).—About 5 mm.

*Petals, fertile flowers*.—Quantity and arrangement: Five in a single whorl. Length: About 3 mm. Width: About 2 mm. Shape: Lanceolate. Apex: Mucronate. Base: Acute. Margin: Entire. Texture and luster, upper and lower surfaces: Smooth, glabrous; matte. Color: When opening, upper surface: Close to 98C. When opening, lower surface: Close to 115B. Fully developed, upper surface: Close to 100A; color becoming closer to N101B with subsequent development. Fully developed, lower surface: Close to 101B; color becoming closer to N115B with subsequent development.

*Petals, sterile flowers*.—To date, petal development has not been observed on the sterile flowers.

*Sepals, fertile flowers*.—Quantity and arrangement: Five in a single whorl. Length: About 1 mm. Width: About 1 mm or less than 1 mm. Shape: Lanceolate. Apex: Acute. Base: Acute. Margin: Entire. Texture and luster, upper and lower surfaces: Smooth, glabrous; matte. Color: When opening, upper surface: Close to 126D. When opening, lower surface: Close to 139C. Fully developed, upper surface: Close to 95C; color becoming closer to N101A with subsequent development. Fully developed, lower surface: Close to 98B; color becoming closer to 133B with subsequent development.

*Sepals, sterile flowers*.—Quantity and arrangement: About eight or more in about one or two whorls. Length: About 1.5 cm. Width: About 1 cm. Shape: Lanceolate. Apex: Mucronate. Base: Acute. Margin: Entire. Texture and luster, upper and lower surfaces: Smooth, glabrous; matte. Color: When opening, upper surface: Close to 193D; when not "blued", close to 65B. When opening, lower surface: Close to 193C; when not "blued", close to 11B. Fully developed, upper surface: Close to 100A; when not "blued", close to 71D; with subsequent development, color becoming closer to N79A and when not "blued", close to 145A. Fully developed, lower surface: Close to 104B; when not "blued", close to 73C; with subsequent development, color becoming closer to N138B and when not "blued", close to 145B.

*Pedicels, fertile flowers*.—Length: About 3 mm. Diameter: About 0.5 mm. Strength: Moderately strong. Aspect: Mostly upright. Texture and luster: Pubescent; matte. Color: Close to 95C.

*Pedicels, sterile flowers*.—Length: About 2.5 cm. Diameter: About 5 mm. Strength: Moderately strong. Aspect: Mostly upright. Texture and luster: Pubescent; matted Color: Close to 95C.

*Reproductive organs, fertile flowers*.—Stamens: To date, stamen development has not been observed on fertile flowers of plants of the new *Hydrangea*. Pistils: Pistil quantity per flower: Three. Pistil length: About 1 mm or less than 1 mm. Stigma shape: Semi-globose. Stigma color: Close to 95B. Style length: About 1 mm or less than 1 mm. Style color: Close to 95B. Ovary color: Close to 95B.

*Reproductive organs, sterile flowers*.—Stamens: To date, stamen development has not been observed on fertile flowers of plants of the new *Hydrangea*. Pistils: Pistil quantity per flower: Three. Pistil length: About 1 mm. Stigma shape: Semi-globose. Stigma color: Bluish. Style length: About 0.5 mm. Style color: Bluish. Ovary color: Bluish.

*Seeds*.—To date, seed development has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to tolerate temperatures from −5° C. to 40° C.

It is claimed:

1. A new and distinct *Hydrangea* plant named 'FRCK 003 S 9' as illustrated and described.

* * * * *